US012295789B2

(12) United States Patent
Jin et al.

(10) Patent No.: US 12,295,789 B2
(45) Date of Patent: May 13, 2025

(54) ULTRASONIC PROBE, SCANNING ASSEMBLY AND ULTRASONIC IMAGING DEVICE

(71) Applicant: GE Precision Healthcare LLC, Wauwatosa, WI (US)

(72) Inventors: Lu Jin, Wuxi (CN); Qiang Yao, Wuxi (CN); Liping Chen, Wuxi (CN); Sheng Xu, Wuxi (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 160 days.

(21) Appl. No.: 17/893,819

(22) Filed: Aug. 23, 2022

(65) Prior Publication Data
US 2023/0061594 A1    Mar. 2, 2023

(30) Foreign Application Priority Data
Aug. 31, 2021    (CN) .......................... 202111016870.4

(51) Int. Cl.
*A61B 8/00* (2006.01)
*A61B 8/08* (2006.01)

(52) U.S. Cl.
CPC .......... *A61B 8/4461* (2013.01); *A61B 8/4218* (2013.01); *A61B 8/4494* (2013.01); *A61B 8/0825* (2013.01)

(58) Field of Classification Search
CPC ... A61B 8/4218; A61B 8/0825; A61B 8/4461; A61B 8/4494
See application file for complete search history.

(56) References Cited

U.S. PATENT DOCUMENTS 4,637,256 A * 1/1987 Sugiyama ............ G10K 11/352
                                                          73/621
7,299,806 B2    11/2007 Lokhandwalla
(Continued)

FOREIGN PATENT DOCUMENTS

CN    205514668 U  *  8/2016
CN    210185606 U     3/2020
(Continued)

OTHER PUBLICATIONS

CN-205514668-U (Year: 2016).*
(Continued)

*Primary Examiner* — Joel Lamprecht
*Assistant Examiner* — Nyrobi Celestine

(57) ABSTRACT

Provided in the present application is an ultrasonic probe, including: an ultrasonic transducer configured to send/receive an ultrasonic signal; a housing including a top plate and a side wall that collectively define a cavity with an opening located below the cavity, wherein a top portion of the ultrasonic transducer is configured to be accommodated in the cavity via the opening; and an elastic element accommodated in the cavity, the elastic element being connected to the top portion of the ultrasonic transducer and the top plate of the housing, and the elastic element being configured to provide an elastic force to the ultrasonic transducer to enable part of the ultrasonic transducer to retract and spring back within the cavity. Further provided in the present application are a scanning assembly including the ultrasonic probe and an ultrasonic imaging device including the scanning assembly.

5 Claims, 7 Drawing Sheets

(56) References Cited

U.S. PATENT DOCUMENTS

| | | | |
|---|---|---|---|
| 8,579,819 B2 | 11/2013 | Wang | |
| 2005/0113684 A1* | 5/2005 | Lokhandwalla | G01H 3/00 |
| | | | 128/915 |
| 2014/0094701 A1* | 4/2014 | Kwartowitz | A61B 8/5223 |
| | | | 600/438 |
| 2014/0121520 A1* | 5/2014 | Wang | A61B 8/403 |
| | | | 600/444 |
| 2015/0094588 A1* | 4/2015 | Summers | A61B 8/0825 |
| | | | 600/445 |
| 2015/0094589 A1 | 4/2015 | Chen | |
| 2016/0001097 A1* | 1/2016 | Cho | A61B 8/44 |
| | | | 601/3 |
| 2019/0150895 A1* | 5/2019 | Tian | A61B 8/4209 |

FOREIGN PATENT DOCUMENTS

| | | | |
|---|---|---|---|
| JP | 04183453 A | 6/1992 | |
| JP | 2018525081 A | 9/2018 | |
| WO | 2005120357 A1 | 12/2005 | |
| WO | WO-2013171671 A1 * | 11/2013 | A61B 8/0825 |

OTHER PUBLICATIONS

JP application 2022-123655 filed Aug. 3, 2022—Office Action issued on Jul. 19, 2023; Machine Translation; 5 pages.
JPH04-183453 English Abstract, retrieved from Espacenet.com Oct. 19, 2023; 1 page.

* cited by examiner

ULTRASONIC PROBE, SCANNING ASSEMBLY AND ULTRASONIC IMAGING DEVICE

CROSS-REFERENCE TO RELATED APPLICATION

This application claims priority to Chinese patent application number 202111016870.4, filed on Aug. 31, 2021, the entirety of which is incorporated herein by reference.

TECHNICAL FIELD

The present application relates to the field of medical imaging, in particular to an ultrasonic probe, a scanning assembly and an ultrasonic imaging device.

BACKGROUND

Ultrasonic imaging is a non-destructive and real-time imaging means, which can be used for scanning a variety of human organs and tissues. One of the examples is an automatic breast ultrasonic imaging system which can perform ultrasonic imaging on the breast of a person receiving a scan. In some examples, the automatic breast ultrasonic imaging system includes a compact scanning assembly. An ultrasonic probe and a driving mechanism capable of driving the ultrasonic probe to move are both integrated in the scanning assembly. Under the action of the driving mechanism, the ultrasonic probe can automatically move in a certain plane (for example, in a horizontal direction) for ultrasonic scanning.

Since the surface of the body tissue to be scanned (for example, the breast) is not flat, the ultrasonic probe produces greater pressure on the higher body tissue as it moves in a plane, for example, in a horizontal direction, which will be uncomfortable for the person receiving a scan, and excessive pressing on the body tissue will also result in poor imaging effect. However, it is difficult to add additional devices in the compact scanning assembly to regulate the pressure of the probe to the body tissue.

SUMMARY

The aforementioned deficiencies, disadvantages, and problems are solved herein, and these problems and solutions will be understood through reading and understanding of the following description.

Provided in some embodiments of the present application is an ultrasonic probe, comprising: an ultrasonic transducer; a housing comprising a top plate and a side wall that collectively define a cavity with an opening located below the cavity, wherein a top portion of the ultrasonic transducer is configured to be accommodated in the cavity via the opening; and an elastic element accommodated in the cavity, the elastic element being connected to the top portion of the ultrasonic transducer and the top plate of the housing, and the elastic element being configured to provide an elastic force to the ultrasonic transducer to enable part of the ultrasonic transducer to retract and spring back within the cavity.

Further provided in some embodiments of the present application is a scanning assembly, comprising: a frame comprising a bottom opening; an ultrasonic probe connected within the frame, the ultrasonic probe comprising: an ultrasonic transducer; a housing including a top plate and a side wall that collectively define a cavity with an opening located below the cavity, wherein a top portion of the ultrasonic transducer is configured to be accommodated in the cavity via the opening; an elastic element accommodated in the cavity, the elastic element being connected to the top portion of the ultrasonic transducer and the top plate of the housing, and the elastic element being configured to provide an elastic force to the ultrasonic transducer to enable part of the ultrasonic transducer to retract and spring back within the cavity; and a film assembly detachably connected to the bottom opening.

Further provided in some other embodiments of the present application is an ultrasonic imaging device, comprising a scanning assembly as described above.

It should be understood that the brief description above is provided to introduce, in simplified form, some concepts that will be further described in the detailed description. The brief description above is not meant to identify key or essential features of the claimed subject matter. The scope is defined uniquely by the claims that follow the detailed description. Furthermore, the claimed subject matter is not limited to implementations that solve any disadvantages noted above or in any section of the present disclosure.

BRIEF DESCRIPTION OF THE DRAWINGS

The present application will be better understood by reading the following description of non-limiting embodiments with reference to the accompanying drawings, where.

DETAILED DESCRIPTION

Specific implementations of the present application will be described below. It should be noted that in the specific description of these implementations, for the sake of brevity and conciseness, this specification may not describe all features of the actual implementations in detail. It should be understood that in the actual implementation process of any implementations, just as in the process of any engineering project or design project, a variety of specific decisions are often made to achieve specific goals of the developer and to meet system-related or business-related constraints, which may also vary from one implementation to another. Furthermore, it should also be understood that although efforts made in such development processes may be complex and tedious, for those of ordinary skill in the art related to the content disclosed in the present application, some design, manufacture or production changes based on the technical content disclosed in the present disclosure are only common technical means, and should not be construed as insufficient content of the present disclosure.

Unless otherwise defined, the technical or scientific terms used in the claims and the description are as they are usually understood by those of ordinary skill in the art to which the present invention pertains. Terms such as "first," "second," and similar terms used in this specification and claims do not denote any order, quantity, or importance, but are only intended to distinguish different constituents. The terms "one" or "a/an" and similar terms do not denote a limitation of quantity, but rather the presence of at least one. The terms "include" or "comprise" and similar terms mean that an element or article preceding the term "include" or "comprise" encompasses elements or articles and their equivalent elements listed after "include" or "comprise," and does not exclude other elements or articles. The terms "connect" or "connected" and similar words are not limited to physical or mechanical connections, and are not limited to direct or indirect connections.

Although some embodiments of the present application are presented in a particular context of human breast ultrasound, it should be understood that the present application is applicable to ultrasonic scanning of any externally accessible human or animal body part (for example, abdomen, legs, feet, arms, or neck).

Figure 1:
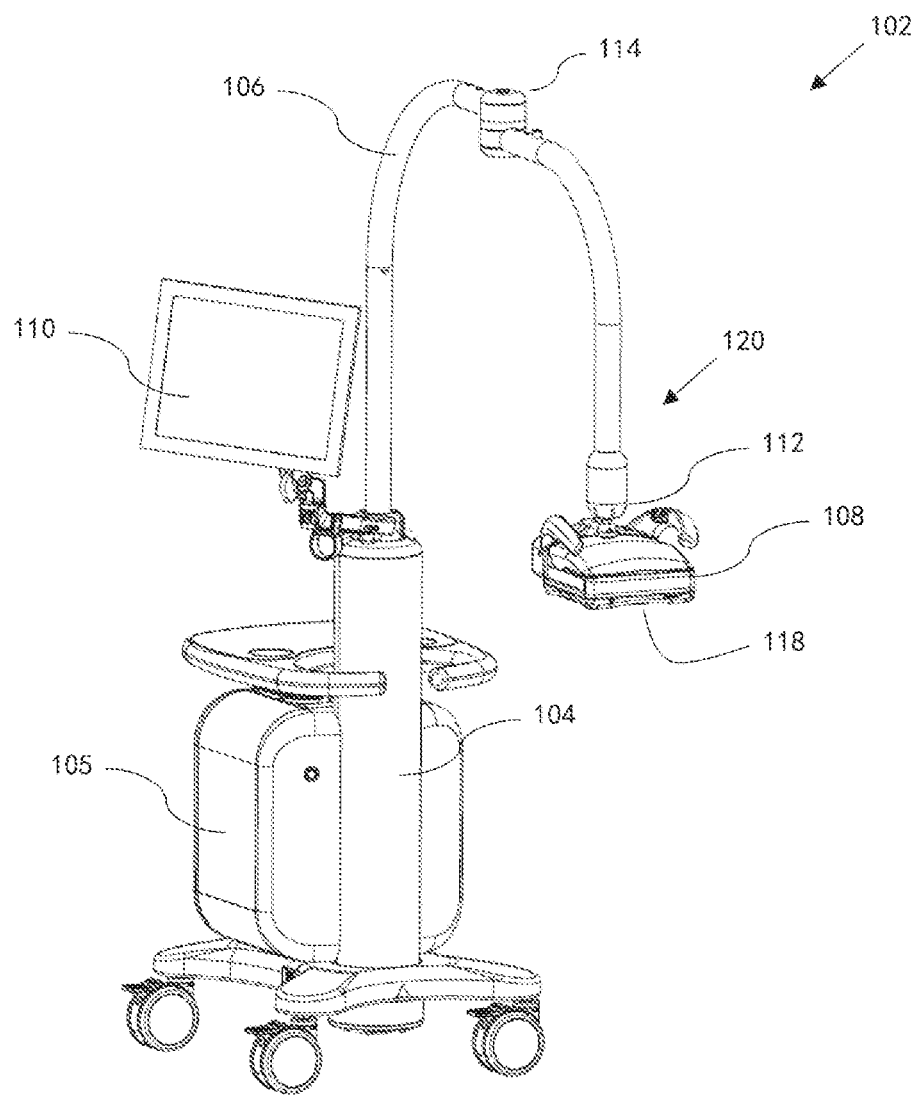
FIG. 1 shows a perspective view of an ultrasonic imaging device according to some embodiments of the present application.

FIG. 1 shows a perspective view of an ultrasonic imaging device 102 according to some embodiments. A body of the ultrasonic imaging device 102 may be a main device, a display 110, an adjustable arm 106, and a scanning assembly 108. The main device may include a body frame 104, an ultrasonic processor housing 105, and an ultrasonic processor inside the ultrasonic processor housing 105. The specific structure of each component will be illustrated in detail below.

The body frame 104, the ultrasonic processor housing 105 containing the ultrasonic processor, a movable and adjustable support arm (for example, an adjustable arm) 106 including a hinge joint 114, the scanning assembly 108 connected to a first end 120 of the adjustable arm 106 by means of a ball and socket connector (for example, a ball joint) 112, and the display 110 connected to the body frame 104. The display 110 is connected to the body frame 104 at a joining point where the adjustable arm 106 enters the body frame 104. Since the display 110 is directly connected to the body frame 104 rather than the adjustable arm 106, the display 110 does not affect the weight of the adjustable arm 106 and a balancing mechanism of the adjustable arm 106. In one example, the display 110 may rotate in horizontal and transverse directions (for example, rotatable around a central axis of the body frame 104), but cannot move vertically. In an alternative example, the display 110 may also be vertically movable. Although FIG. 1 illustrates the display 110 being connected to the body frame 104, in other examples, the display 110 may be connected to different components of the ultrasonic imaging device 102, such as, connected to the ultrasonic processor housing 105, or positioned away from the ultrasonic imaging device 102.

In one embodiment, the adjustable arm 106 is configured and adapted such that the pressing/scanning assembly 108 (i) is neutrally buoyant in space, or (ii) has a light net downward weight (for example, 1-2 kg) for pressing the breast, while allowing easy user operation. In an alternative embodiment, the adjustable arm 106 is configured such that the scanning assembly 108 is neutrally buoyant in space during positioning of a scanner on tissue of a patient. Then, after the scanning assembly 108 is positioned, internal components of the ultrasonic imaging device 102 may be adjusted to apply a desired downward weight for pressing the breast and improving the image quality. In one example, the downward weight (for example, a force) may be in a range of 2-11 kg.

As described above, the adjustable arm 106 includes the hinge joint 114. The hinge joint 114 divides the adjustable arm 106 into a first arm portion and a second arm portion. The first arm portion is connected to the scanning assembly 108 and the second arm portion is connected to the body frame 104. The hinge joint 114 allows the second arm portion to rotate relative to the second arm portion and the body frame 104. For example, the hinge joint 114 allows the scanning assembly 108 to translate transversely and horizontally, but not vertically, relative to the second arm portion and the body frame 104. In such manner, the scanning assembly 108 can rotate toward the body frame 104 or away from the body frame 104. However, the hinge joint 114 is configured to allow the entire adjustable arm 106 (for example, the first arm portion and the second arm portion) to move vertically together as a whole (for example, translating upward and downward along with the body frame 104).

The scanning assembly 108 may include a film assembly 118 having a film that is in a substantially tensioned state to be at least partially attached, for pressing the breast. The film assembly 118 has a bottom surface for contacting the breast, and when the bottom surface is in contact with the breast, the transducer sweeps over a top surface of the film to scan the breast. In one example, the film is a tensioned fabric sheet.

Optionally, the adjustable arm may include a potentiometer (not shown) to allow position and direction sensing performed by the pressing/scanning assembly 108, or may use other types of position and direction sensing (such as gyroscope, magnetic, optical, and radio frequency (RF)). A fully functional ultrasonic engine may be provided within the ultrasonic processor housing 105, and is configured to drive the ultrasonic transducer, and generate volumetric breast ultrasound data from a scan in conjunction with related position and orientation information. In some examples, volumetric scan data may be transmitted to another computer system by using any of a variety of data transmission methods known in the art so as to be further processed, or the volumetric scan data may be processed by the ultrasonic engine. A general-purpose computer/processor integrated with the ultrasonic engine may further be provided for general user interface and system control. The general-purpose computer may be a self-contained stand-alone unit, or may be remotely controlled, configured, and/or monitored by remote stations connected across networks.

Figure 2:
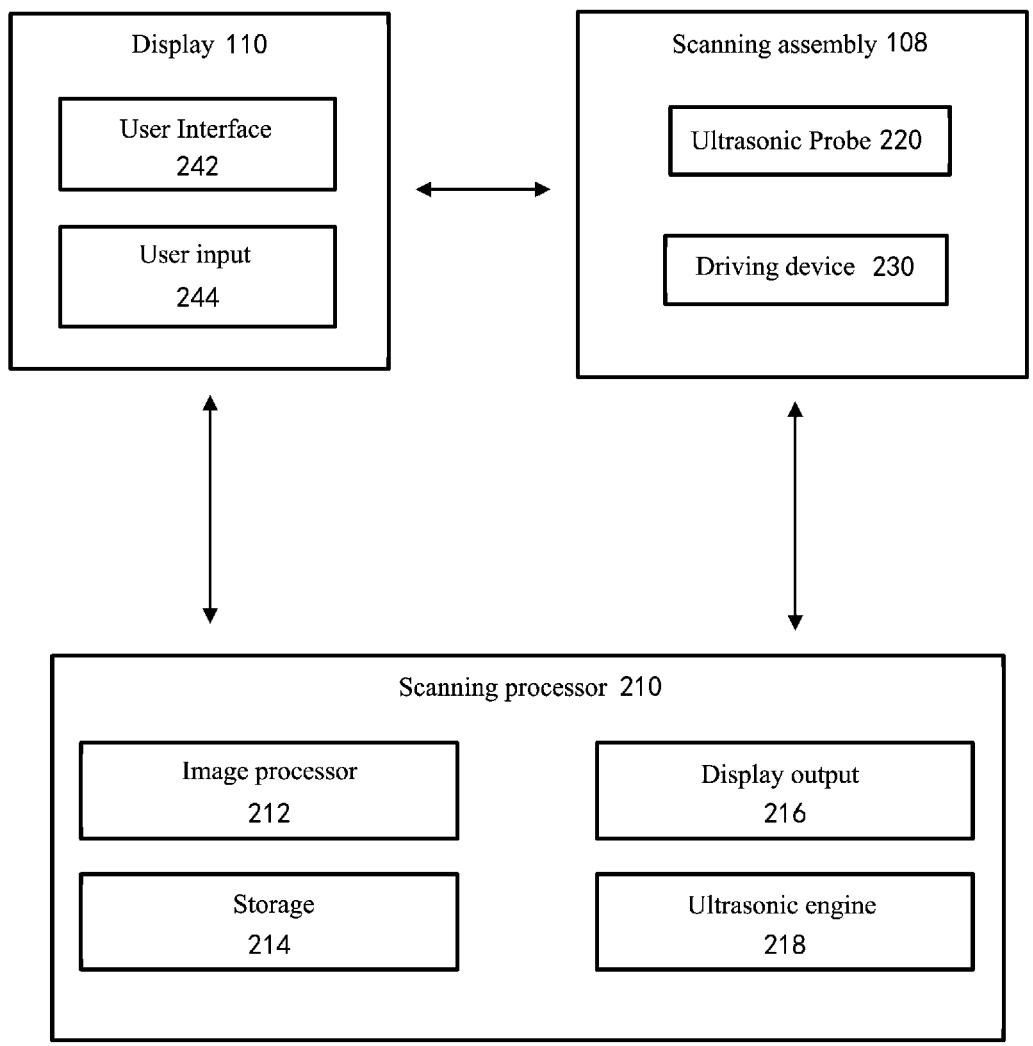
FIG. 2 shows a schematic block diagram of various system components of an ultrasonic imaging device according to some embodiments of the present application.

FIG. 2 is a block diagram 200 schematically showing various system components of the ultrasonic imaging device 102, including a scanning assembly 108, a display 110, and a scanning processor 210. In one example, the scanning processor 210 may be included in the ultrasonic processor housing 105 of the imaging device 102. As shown in the embodiment of FIG. 2, the scanning assembly 108, the display 110, and the scanning processor 210 are independent components that communicate with each other; however, in some embodiments, one or more of these components may be integrated (for example, the display and the scanning processor may be included in a single component).

First, referring to the scanning assembly 108, the scanning assembly 108 includes at least an ultrasonic probe 220 and a driving device 230. The ultrasonic probe 220 includes a transducer array of transducer elements, such as a piezoelectric element, which converts electrical energy into ultrasonic waves and then detects reflected ultrasonic waves.

The scanning assembly 108 may communicate with the scanning processor 210 to send raw scan data to an image processor. The scanning assembly 108 may optionally communicate with the display 110 so as to indicate a user to reposition the scanning assembly as described above, or to receive information from the user (via a user input unit 244).

Now referring to the scanning processor 210, and the scanning processor includes an image processor 212, a memory 214, a display output 216, and an ultrasonic engine 218. The ultrasonic engine 218 may drive activation of the transducer elements of the ultrasonic probe 220, and in some embodiments, the driving device 230 may be activated. Furthermore, the ultrasonic engine 218 may receive raw image data (for example, ultrasonic echoes) from the scanning assembly 108. The raw image data may be sent to the image processor 212 and/or a remote processor (for example, via a network) and be processed to form a displayable image of a tissue sample. It should be understood that in some embodiments, the image processor 212 may be included in the ultrasonic engine 218.

Information may be transmitted from the ultrasonic engine 218 and/or the image processor 212 to a user of the imaging device 102 via the display output 216 of the scanning processor 210. In an example, the user of the scanning device may include an ultrasonic technician, a nurse, or a physician. For example, a processed image of scanned tissue may be sent to the display 110 via the display output 216. In another example, information related to parameters of the scanning (such as the progress of scanning) may be sent to the display 110 via the display output 216. The display 110 may include a user interface 242 configured to display images or other information to the user. Furthermore, the user interface 242 may be configured to receive input from the user (such as by means of the user input 244) and send the input to the scanning processor 210. In one example, the user input 244 may be a touch screen of the display 110. However, other types of user input mechanisms are also possible, such as a mouse, a keyboard, and the like.

The scanning processor 210 may further include the memory 214. The storage 214 may include movable and/or permanent devices, and may include an optical memory, a semiconductor memory, and/or a magnetic memory. The storage 214 may include a volatile, non-volatile, dynamic, static, read/write, read only, random access, sequential access, and/or additional memory. The storage 214 may store non-transitory instructions executable by a controller or processor (such as the controller 218 or the image processor 212) so as to perform one or more methods or routines as described below. The storage 214 may store raw image data received from the scanning assembly 108, processed image data received from the image processor 212 or the remote processor, and/or additional information.

Figure 3:
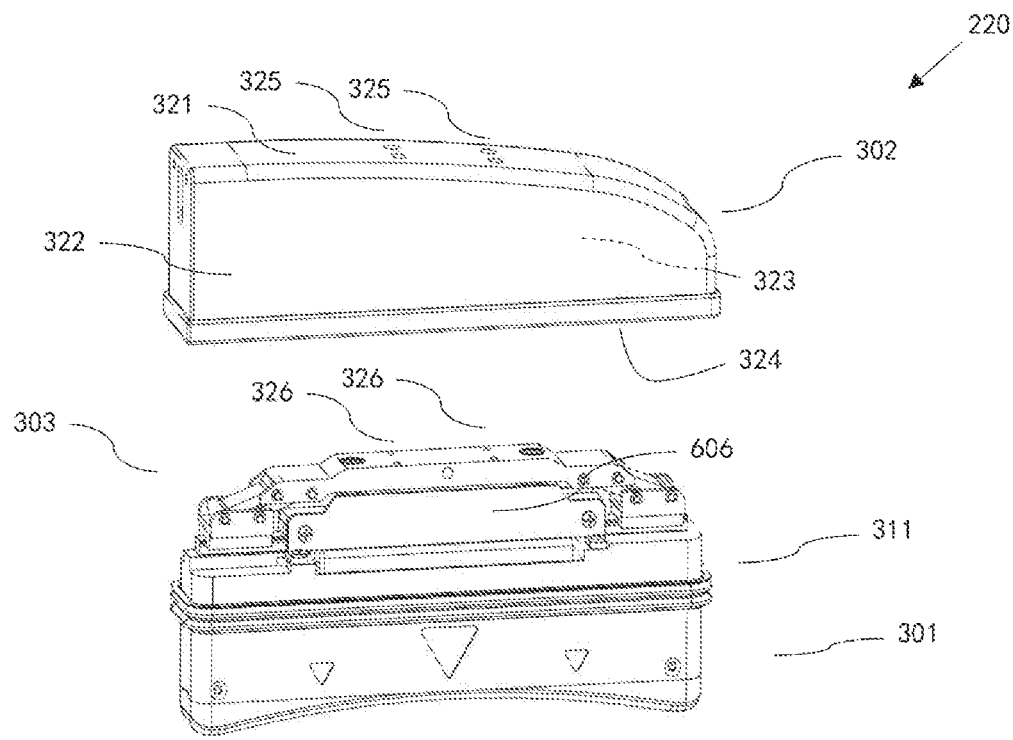
FIG. 3 shows a perspective view of an ultrasonic probe with a housing in an unassembled state according to some embodiments of the present application.
Figure 4:
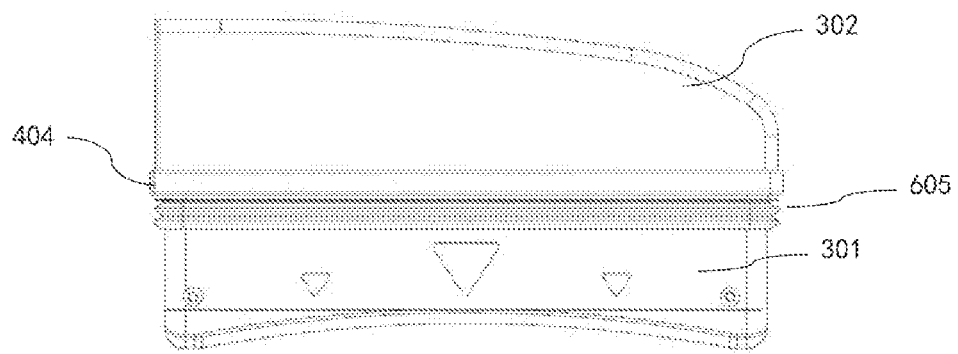
FIG. 4 shows a perspective view of an ultrasonic probe with a housing in an assembled state according to some embodiments of the present application.

The structure of the ultrasonic probe in some embodiments of the present application is described in detail below. Refer to FIG. 3 and FIG. 4. FIG. 3 shows a perspective view of an ultrasonic probe 220 with a housing 302 in an unassembled state according to some embodiments of the present application. FIG. 4 shows a perspective view of an ultrasonic probe 220 with a housing 302 in an assembled state according to some embodiments of the present application.

As shown in FIG. 3 and FIG. 4, the ultrasonic probe 220 includes an ultrasonic transducer 301. The ultrasonic transducer 301 is configured to send/receive an ultrasonic signal. Also included is a housing 302. The housing 302 includes a top plate 321 and a side wall 322. The top plate 321 and the side wall 322 of the housing 302 define a cavity 323. The housing includes an opening 324 located below the cavity. A top portion 311 of the ultrasonic transducer 301 is accommodated in the cavity 323 via the opening 324. The ultrasonic probe 220 further includes an elastic element 303 accommodated in the cavity 323. The elastic element 303 is connected to the top portion 311 of the ultrasonic transducer 301 and the top plate 321 of the housing 302. The elastic element 303 is configured to provide an elastic force to the ultrasonic transducer 301 to enable part of the ultrasonic transducer 301 to retract and spring back within the cavity.

The configuration mode of the ultrasonic probe 220 described above in the present application enables the ultrasonic probe 220 to be retractable. In such a configuration mode, when the ultrasonic probe 220 moves to the raised body surface during the ultrasonic scanning process, the ultrasonic probe 220 can compress the elastic element 303 to retract a certain distance due to receiving a greater support force. This can reduce the pressure on a person receiving a scan and function as buffering, greatly increasing the user experience. Also, when performing the scanning process, the elastic ultrasonic probe 220 would not cause the tissue being scanned to deform easily under great pressure and thus affect the quality of scanning. Furthermore, more importantly, in special automatic ultrasonic scanning scenario, the ultrasonic probe 220 needs to be installed and used in the scanning assembly. The space it can occupy is very limited. In the present application, the housing 302 originally configured to accommodate electrical connecting elements of the ultrasonic transducer 301, such as a printed circuit board (PCB) 606, cables and other components, is configured to accommodate the size of the top portion 311 of the ultrasonic transducer 301, and the elastic element 303 is configured on the top plate of the housing 302 and the top portion 311 of the ultrasonic transducer 301. The ultrasonic probe 220 can be retractable in the vertical direction without requiring too much additional volume, and the connection between the housing 302 and the ultrasonic transducer 301 is also tight.

Still referring to FIG. 3. The top plate 321 of the housing 302 and the elastic element 303 may be connected in any manner. For example, a through hole 325 may be formed in the top plate 321, and a screw hole 326 may be formed in the elastic element 303 at a position corresponding to the through hole 325. In this way, the housing 302 and the elastic element 303 can be connected by screws (not shown). The connected elastic element 303 can be fully accommodated inside the cavity 323 of the housing 302. Similarly, the elastic element 303 can also be connected to the top portion 311 of the ultrasonic transducer 301 by screws. It can be understood that the above connection modes can also be other modes, and details will not be described herein again.

Referring to FIG. 4 below, the overall structure is compact when the ultrasonic probe 220 is in the assembled state. At this time, the elastic element 303 is invisible due to being hidden inside the housing 302. When scanning the surface, the ultrasonic transducer 301 will be subjected to an upward pressure. Further, due to the presence of the elastic element 303, the ultrasonic transducer 301 can move upward.

The specific construction of the elastic element 303 may be varied. A detailed exemplary description of the structure thereof is given below. By way of exemplary description, the progress of the elastic element 303 of the present application compared with the prior art can also be better illustrated.

Figure 5:
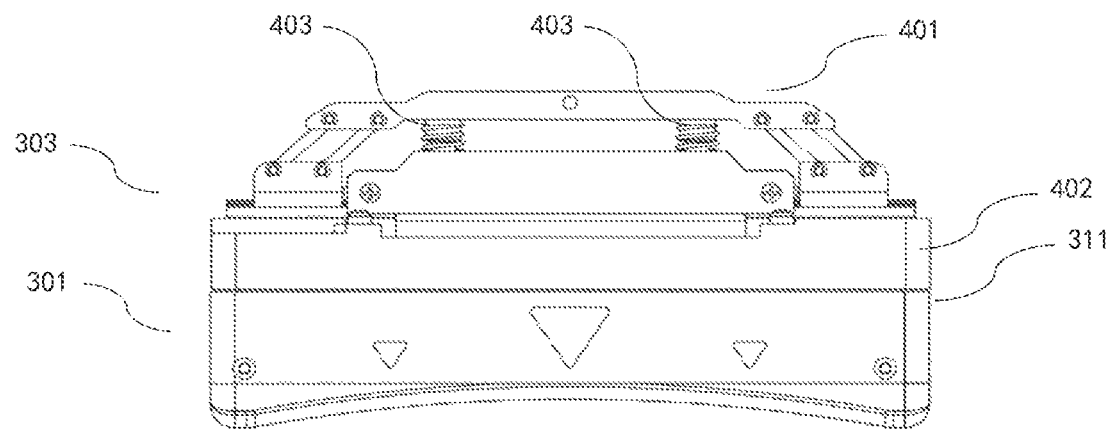
FIG. 5 shows a schematic diagram of an ultrasonic probe with a housing removed according to some embodiments of the present application.

FIG. 5 shows a schematic diagram of an ultrasonic probe 220 with a housing 302 removed according to some embodiments of the present application. As shown in FIG. 5, the elastic element 303 may include a first base 401. The first base 401 is connected to the top plate of the housing 302 (not shown in FIG. 5). The elastic element 303 further includes a second base 402. The second base 402 is connected to the top portion 311 of the ultrasonic transducer 301. In some examples, the top portion 311 may be sleeved inside the second base 402. The elastic element 303 further includes springs 403. The spring 403 is disposed between the first base 401 and the second base 402 to achieve an elastic connection of the first base 401 and the second base 402.

Through the arrangement mode of the first base 401 and the second base 402, a larger contact area can be provided between the elastic element 303, the ultrasonic transducer 301 and the housing 302. In this way, when the ultrasonic transducer 301 extends and retracts in the vertical direction, the motion path thereof can be more stable and better fit the curve of the surface being scanned, thereby ensuring the imaging quality.

The spring 403 is configured to provide a rebound force between the first base 401 and the second base 402, and it can be understood that the rebound force finally acts on the ultrasonic transducer 301. Therefore, a suitable rebound force to the ultrasonic transducer 301 can be determined by selecting a spring 403 with a suitable stiffness coefficient, ensuring the user experience and imaging to be desirable.

In some embodiments, when there is no external force acting on the ultrasonic transducer 301, the spacing between the first base 401 and the second base 402 is configured to be less than the original length of the spring 403. In this way, the spring 403 is always in a compressed state. Even without external force, the spring can provide a certain elastic force for the ultrasonic transducer 301 to avoid the oscillation of the ultrasonic transducer 301.

In addition, the quantity of springs 403 may be freely selected. As shown in FIG. 4, the quantity of the springs may be two, and the springs are symmetrically disposed at positions close to two ends of the first base 401. In this way, the spring 403 can provide a more uniform rebound force, so as to prevent the ultrasonic transducer from being stuck in the process of extending and retracting in the vertical direction and thus affecting the imaging.

Figure 6:
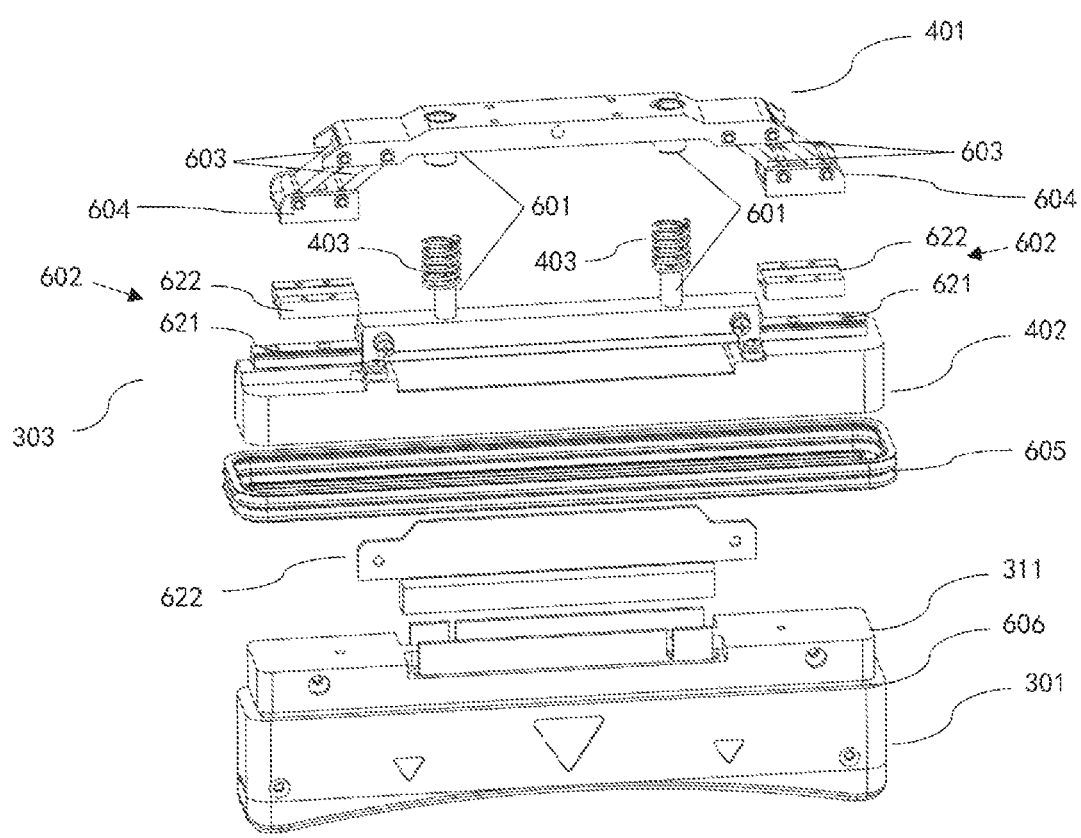
FIG. 6 shows a perspective exploded view of an ultrasonic probe according to some embodiments of the present application.

In some other embodiments of the present application, the structure of the elastic element 303 is further optimized. FIG. 6 shows a perspective exploded view of an ultrasonic probe 220 according to some embodiments of the present application.

As shown in FIG. 6, the elastic element 303 may further include guide posts 601. The guide posts 601 are disposed between the first base 401 and the second base 402. The spring 403 is sleeved on the outer periphery of the guide post 601.

In such a configuration mode, the guidance of the spring 403 in the process of compression and extension can be achieved, thereby avoiding distortion or displacement of the spring resulting in failure. The guide posts 601 may be configured in various modes. For example, the guide posts may include a rod-like structure and a sleeve structure arranged opposite to each other in a vertical direction. As shown in FIG. 6, the rod-like structure and the sleeve structure are respectively disposed on the two opposite surfaces of the first base 401 and the second base 402, and the sizes thereof are configured to match each other, that is, the inner diameter of the sleeve is slightly larger than the outer diameter of the rod-like structure, so as to achieve guidance.

The ultrasonic probe 220 can perform linear motion in a horizontal direction when driven by the driving device in the scanning assembly, and likewise, the ultrasonic transducer 301 of the ultrasonic probe 220 performs linear motion in the horizontal direction. The ultrasonic transducer 301 that performs linear motion performs tomographic scanning on the tissue being imaged (for example, the breast) in a vertical direction, and obtains a large number of two-dimensional cross-sectional ultrasonic images of the tissue in the vertical direction. Due to the linear motion described above, the imaging planes of these two-dimensional images are parallel to each other, so a three-dimensional ultrasonic image can be obtained by synthesis.

The inventors found that if the ultrasonic transducer 301 oscillates in the direction of motion, the two-dimensional images obtained by tomographic scanning will no longer be parallel. The three-dimensional ultrasonic image obtained by synthesis is thus inevitably affected. In particular, the retractable ultrasonic probe is prone to oscillate during movement. In this regard, the inventors have made improvements.

Still refer to FIG. 6. Optionally, the elastic element 303 may further include a slide rail assembly 602 and connecting rods 603. The slide rail assembly 602 includes a guide rail 621 and slide blocks 622 that are slidably connected to the guide rail. The slide rail assembly 602 is disposed at two ends of the second base 402. Further, the connecting rods 603 are disposed at two ends of the first base 401. The connecting rods 603 are rotatably connected to the first base 401 and the slide blocks 622.

Such an arrangement has a variety of advantages. Due to the tight fit between the guide rail 621 and the slide blocks 622, the ultrasonic transducer 301 does not oscillate in the horizontal movement direction when being driven to move in the horizontal direction, thereby not affecting the imaging quality. This is critical for an ultrasonic probe that is movable itself. Also, the slide rail assembly 602, which includes the guide rail 621 and the slide blocks 622, and the connecting rods 603, as a whole cooperating with each other, can also function to limit the extension and retraction of the ultrasonic transducer 301 in the vertical direction. The connection of the slide rail assembly 602 and the connecting rods 603 ensures that the first base 401 and the second base 402 will not be disengaged during the vertical movement, that is, the connection functions to limit the ultrasonic transducer 301 in the extended state. Moreover, when the spring 403 is compressed to a certain extent, the slide rail assembly 602 and the connecting rods 603 reach the limit of sliding due to angular rotation and other reasons, that is, the slide rail assembly and the connecting rods function to limit the ultrasonic transducer 301 in the compressed state.

In addition, in some embodiments, two connecting rods 603 may be provided at each end of the first base 401. The two connecting rods 603 at each end of the first base 401 are rotatably connected to the slide block 622 through a base plate 604.

Such an arrangement makes the rotational connection of the connecting rods 603 more stable. In addition, by additionally arranging the base plate 604, the assembly of the slide rail assembly 602 and the connecting rods 603 is more convenient. In assembly, the slide block 622 can be sleeved on the guide rail 621 from the end of the guide rail 621 first, and then the base plate 604 can be installed in alignment with the slide block 622. The installation mode may be diverse. For example, the installation may be performed by screws. Details will not be described herein again.

It can be seen from the above that the above solution disclosed in the present application enables the ultrasonic probe to have the advantages of compact structure and preventing oscillation in the direction of motion while ensuring the extension and retraction in the vertical direction. Further, the inventors also found that the waterproof performance of the retractable ultrasonic probe is a challenge. The ultrasonic transducer needs a coupling agent during use, and needs to be sterilized with a liquid such as alcohol after use. The movable probe means that there is a larger gap between the moving components.

To address the problems described above, the present application has made improvements in some embodiments. In some embodiments, the ultrasonic probe 220 of the present application may also include an elastic seal ring 605. As shown in FIG. 4 and FIG. 6, the elastic seal ring 605 includes a corrugated elastic material. The elastic seal ring 605 is sleeved on the top portion 311 of the ultrasonic transducer 301 to fill a gap between the top portion 311 of the ultrasonic transducer 301 and the side wall 322 of the housing 302.

The corrugation of the elastic seal ring 605 makes it compressible. The corrugated elastic seal ring can be compressible as the ultrasonic transducer 301 extends and retracts in the vertical direction without damage. Also, the corrugated elastic seal ring can provide a good sealing effect on the gap between the ultrasonic transducer 301 and the housing 302, preventing liquid from corroding the elastic element 303 and other electrical elements such as the PCB 606 in the housing. The material of the elastic seal ring 605 is not limited. For example, the elastic seal ring may be made of a high polymer material, such as rubber and latex.

In some embodiments, the top portion 311 of the ultrasonic transducer 301 and the side wall 322 of the housing 302 are each provided with an engaging groove. The upper and lower openings of the elastic seal ring 605 are engaged with the engaging grooves. Specifically, reference may be made to FIG. 4 and FIG. 6. The side wall 322 of the housing 302, for example the bottom of the side wall 322, may be provided with an engaging groove 404. Correspondingly, the top portion 311 of the ultrasonic transducer 301 may be provided with another engaging groove 606. The upper and lower openings of the elastic seal ring 605 are engaged with the engaging grooves. For example, the upper and lower openings may be inwardly folded, so that the openings can be fit into the engaging grooves.

Such an arrangement can ensure that the elastic seal ring 605 does not move or fall off during the movement of the ultrasonic transducer 301, resulting in failure of the sealing state.

Figure 7:
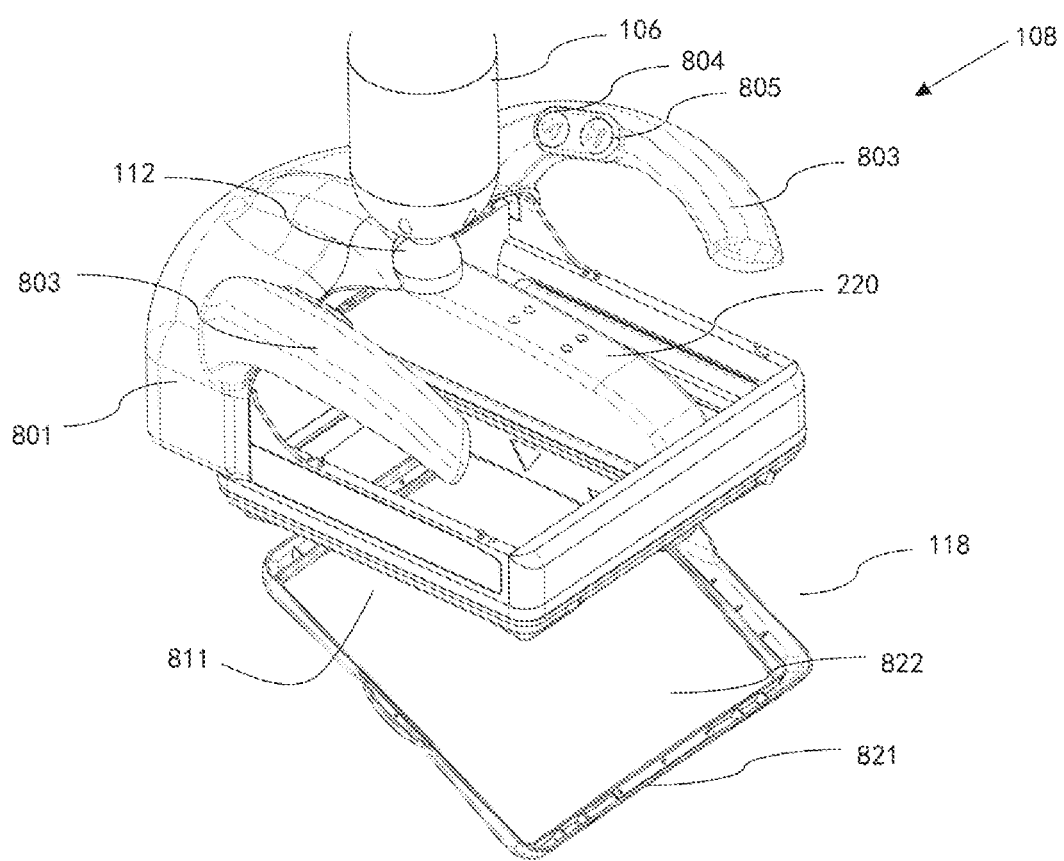
FIG. 7 shows a perspective view of a scanning assembly according to some embodiments of the present application.

Further provided in some embodiments of the present application is a scanning assembly 108. FIG. 7 shows a perspective view of a scanning assembly 108 according to some embodiments of the present application.

The scanning assembly 108 may include a frame 801. The frame 801 includes a bottom opening 811. The scanning assembly further includes the ultrasonic probe 220 of any of the above embodiments, and the ultrasonic probe 220 is connected within the frame 801. The scanning assembly 108 further includes a film assembly 118. The film assembly 118 is detachably connected to the bottom opening 811.

As can be seen from FIG. 7, the overall structure of the scanning assembly 108 is very compact, and the structure of the ultrasonic probe 220 described in any of the above embodiments of the present application does not occupy too much volume, and can be easily assembled in the frame of the scanning assembly 108 for ultrasonic scanning. In the scanning process, since the ultrasonic probe 220 is configured to be retractable in the vertical direction, it can conform to the shape of the surface being scanned in the scanning process in the horizontal direction. In this way, the comfort level of the person receiving a scan can be improved, and since the ultrasonic probe 220 will not cause excessive pressure on the body, the imaging quality can also be improved. It can be understood that the horizontal direction and the up-down direction (or vertical direction) herein refer to the direction in which the ultrasonic probe 220 is driven to move when performing scanning and the direction in which the transducer of the ultrasonic probe 220 extends and retracts, respectively.

Further, the film assembly 118 includes an outer frame 821 and a film 822. The film 822 is disposed within the outer frame 821. The outer frame 821 is detachably connected to the bottom opening 811.

The film assembly 118 can be matched to the ultrasonic probe 220. The film 822 of the film assembly 118 can function to press and secure the tissue being scanned, thereby facilitating smooth movement and high-quality imaging of the ultrasonic probe 220 on the surface of the tissue being scanned. It can be understood that in the ultrasonic imaging process, one surface of the film 822 can contact the ultrasonic transducer of the ultrasonic probe 220, and the other surface can contact the tissue being scanned. In the presence of the coupling agent, an acoustic signal transmits through the film 822 with less attenuation.

In addition to the above structures, the scanning assembly 108 of the present application may further include other components. These components are described in detail below. However, it should be noted that as an optional example, the following components are not required.

Still refer to FIG. 7. The scanning assembly 108 further includes two handles 803 arranged on the frame 801. The two handles 803 oppose each other across a transverse axis of the scanning assembly 108, and the transverse axis is centered on the adjustable arm 106 and defined relative to the transverse axis. The frame 801 may have a rectangular opening. In another example, the frame 801 may have another shape, such as a square having a square opening. In addition, the frame 801 has a thickness defined between an inner periphery and an outer periphery of the frame 801.

The two handles 803 are configured to move the scanning assembly 108 in space and to position the scanning assembly 108 on a tissue (e.g., on a patient). In an alternative embodiment, the scanning assembly 108 may not include the handles 803. In an example, the handles 803 may be formed integrally with the frame 801. In another example, the handles 803 and the frame 801 may be formed separately.

As shown in FIG. 7, the scanning assembly 108 is connected to the adjustable arm 106 by means of the ball joint 112 (e.g., a ball and socket connector). Specifically, a top dome portion of the frame 801 is connected to the ball joint 112. The top of the frame 801 includes a depression forming a socket, and a ball of the ball joint 112 is fit in the socket. The ball joint 112 is movable in multiple directions. For example, the ball joint 112 provides rotational motion of the scanning assembly relative to the adjustable arm 106. The ball joint 112 includes a locking mechanism for locking the ball joint 112 in place, thereby holding the scanning assembly 108 stationary relative to the adjustable arm 106. Furthermore, the ball joint 112 may also be configured to only rotate but not to move in multiple directions, such as oscillating.

In addition, as shown in FIG. 7, the handles 803 are further provided with buttons for controlling scanning and adjusting the scanning assembly 108. Specifically, the above buttons may include a first weight adjustment button 804 and a second weight adjustment button 805. The first weight adjustment button 804 may reduce a load applied to the scanning assembly 108 from the adjustable arm 106. The second weight adjustment button 805 may increase a load applied to the scanning assembly 108 from the adjustable arm 106. The above increase or decrease may be controlled based on the magnitude of the pressure displacement of the adjustable arm 106 with respect to the scanning assembly 108. Increasing the load applied to the scanning assembly 108 may increase the pressure and the amount of pressing applied to the tissue on which the scanning assembly 108 is placed. Furthermore, increasing the load applied to the scanning assembly increases the effective weight of the scanning assembly on the tissue to be scanned. In one example, increasing the load may press a tissue of a patient, such as a breast. In such way, varying amounts of pressure (e.g., load) may be applied consistently with the scanning assembly 108 during scanning in order to obtain high-quality images by using the ultrasonic probe 220.

Prior to the scanning process, a user (e.g., an ultrasonic technician or physician) may position the scanning assembly 108 on a patient or a tissue. Once the scanning assembly 108 is positioned, the user may adjust the pressure (e.g., adjusting an amount of pressing) of the scanning assembly 108 on the patient by using the first weight adjustment button 804 and/or the second weight adjustment button 805. The user may then initiate a scanning process by means of additional control (e.g., buttons of another handle) on the handles 803.

Figure 8:
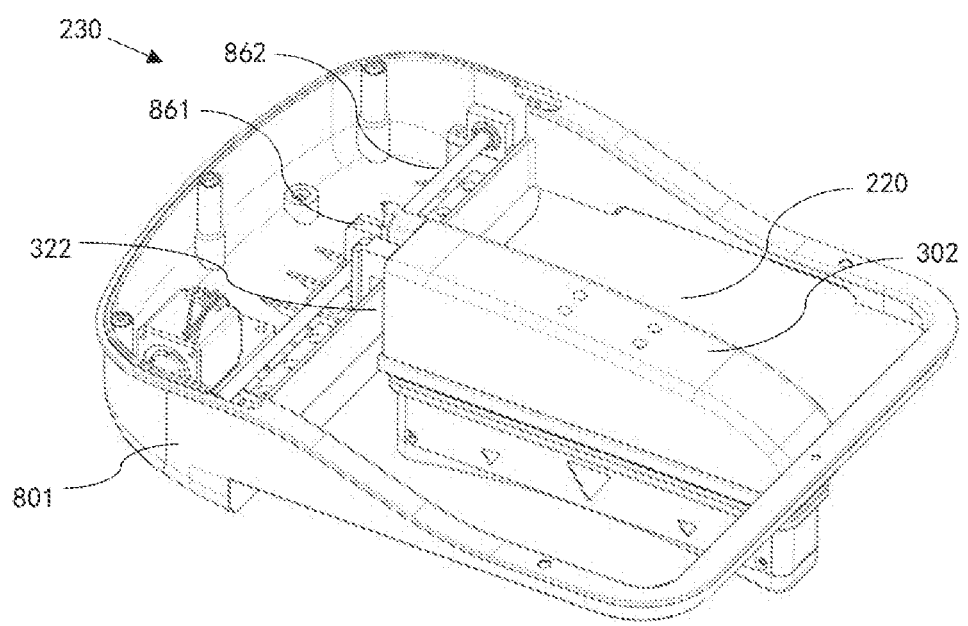
FIG. 8 shows a schematic diagram of a connection relationship between a driving device and an ultrasonic probe according to some embodiments of the present application.

The automatic scanning of the ultrasonic probe may be achieved by means of a driving device inside the frame 801 of the scanning assembly 108. FIG. 8 shows a schematic diagram of a connection relationship between a driving device 230 and an ultrasonic probe 220 according to some embodiments of the present application. The top structure of the frame 801 of the scanning assembly 108 is removed in this figure.

The driving device 230 is disposed in the frame 801. The driving device is connected to the side wall 322 of the housing 302 of the ultrasonic probe 220 to drive the ultrasonic probe 220 to move. In this way, the automatic scanning of the ultrasonic probe 220 for the tissue to be scanned may be achieved without the need for the scanner to hold and move the probe.

In some embodiments, the driving device 230 includes a motor 861 and a lead screw 862. The lead screw 862 is disposed horizontally in the frame. The motor 861 is connected to the side wall 322 of the housing 302. The motor and the lead screw are movably connected to drive the ultrasonic probe to move in a horizontal direction.

The mode in which the lead screw 862 is disposed in the frame 801 is not limited. For example, two ends of the lead screw may be fixedly connected to two side walls of the frame 801. The connection mode between the motor 861 and the housing of the ultrasonic probe 220 is also not limited. For example, the motor 861 may be fixedly connected to the side wall 322 by means of a screw structure. The motor 861 is movably connected to the lead screw 862 so as to drive the ultrasonic probe 220 to move.

The motor 861 drives the ultrasonic probe 220 to perform reciprocating movement in a direction of the lead screw by means of rotation of an internal output shaft in different directions (e.g., clockwise or counterclockwise direction) or by using the output shaft to drive a gear to movably connect the lead screw 862, thereby automatically performing ultrasonic scanning. It should be noted that other motion modes are also allowed. For example, the ultrasonic probe 220 is driven to rotate around a certain center of circle. Although the internal structure of the motor 861 is not directly shown in FIG. 8, those skilled in the art should know that all modes that establish the movable connection between the motor 861 and the lead screw 862 are allowed.

In addition, further disclosed in some embodiments of the present application is an ultrasonic imaging device, including the scanning assembly described in any of the above embodiments.

In some embodiments, the ultrasonic imaging device may include an adjustable arm and a main device as shown in FIG. 1. The scanning assembly is connected to one end of the adjustable arm; the main device is connected to the other end of the adjustable arm.

The purpose of providing the above specific embodiments is to allow the content disclosed in the present application to be understood more thoroughly and comprehensively, but the present application is not limited to these specific embodiments. Those skilled in the art should understand that various modifications, equivalent replacements, and changes can also be made to the present application and should be included in the scope of protection of the present application as long as these changes do not depart from the spirit of the present application.

The invention claimed is:

1. An ultrasonic probe, comprising:
   an ultrasonic transducer;
   a housing comprising a top plate and a side wall that collectively define a cavity with an opening located below the cavity, wherein a top portion of the ultrasonic transducer is configured to be accommodated in the cavity via the opening; and
   an elastic element accommodated in the cavity, the elastic element being connected to the top portion of the ultrasonic transducer and the top plate of the housing, and the elastic element being configured to provide an elastic force to the ultrasonic transducer to enable part of the ultrasonic transducer to retract and spring back within the cavity,
   wherein the elastic element comprises:
   a first base connected to the top plate of the housing;
   a second base connected to the top portion of the ultrasonic transducer;
   springs disposed between the first base and the second base to achieve an elastic connection of the first base and the second base;
   a slide rail assembly comprising a guide rail and slide blocks that are slidably connected to the guide rail, the slide rail assembly being disposed at two ends of the second base; and
   connecting rods disposed at two ends of the first base, the connecting rods being rotatably connected to the first base and the slide blocks.

2. The ultrasonic probe according to claim 1, wherein the elastic element further comprises: guide posts disposed between the first base and the second base, wherein each of the springs being sleeved on an outer periphery of one of the guide posts.

3. The ultrasonic probe according to claim 1, wherein
two connecting rods are provided at each end of the first base, and the two connecting rods at each end of the first base are rotatably connected to the slide blocks by means of a base plate.

4. The ultrasonic probe according to claim 1, further comprising:
an elastic seal ring comprising a corrugated elastic material, the elastic seal ring being sleeved on the top portion of the ultrasonic transducer to fill a gap between the top portion of the ultrasonic transducer and the side wall of the housing.

5. The ultrasonic probe according to claim 4, wherein
the top portion of the ultrasonic transducer and the side wall of the housing are each provided with an engaging groove, and upper and lower openings of the elastic seal ring are engaged with the engaging grooves.

* * * * *